(12) United States Patent
Li et al.

(10) Patent No.: US 6,885,724 B2
(45) Date of Patent: Apr. 26, 2005

(54) RADIOGRAPHIC TOMOSYNTHESIS IMAGE ACQUISITION UTILIZING ASYMMETRIC GEOMETRY

(75) Inventors: Baojun Li, Waukesha, WI (US); Abdulrahman Al-Khalidy, Clifton Park, NY (US); Jeffrey W. Eberhard, Albany, NY (US); Stephen W. Metz, Greenfield, WI (US); Bernhard Erich Hermann Claus, Niskayuna, NY (US); Vianney Pierre Battle, Milwaukee, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/646,023

(22) Filed: Aug. 22, 2003

(65) Prior Publication Data

US 2005/0041768 A1 Feb. 24, 2005

(51) Int. Cl.⁷ .............................................. G01N 23/00
(52) U.S. Cl. ......................................................... 378/2
(58) Field of Search .............................................. 378/2

(56) References Cited

U.S. PATENT DOCUMENTS

| | | | | |
|---|---|---|---|---|
| 3,746,872 A | * | 7/1973 | Ashe et al. ..................... 378/2 |
| 4,416,018 A | * | 11/1983 | Curth et al. .................... 378/2 |
| 5,473,653 A | * | 12/1995 | Harding ......................... 378/2 |
| 5,511,106 A | | 4/1996 | Doebert et al. |
| 5,668,844 A | * | 9/1997 | Webber .......................... 378/2 |
| 6,324,249 B1 | * | 11/2001 | Fazzio .......................... 378/22 |
| 6,570,954 B1 | | 5/2003 | Rasche et al. |
| 6,633,626 B1 | * | 10/2003 | Trotter et al. ................. 378/62 |
| 6,751,284 B1 | * | 6/2004 | Claus et al. ................... 378/22 |

* cited by examiner

Primary Examiner—Craig E. Church
Assistant Examiner—Thomas R. Artman
(74) Attorney, Agent, or Firm—Christopher L. Bernard, Esq.

(57) ABSTRACT

Systems and methods that utilize asymmetric geometry to acquire radiographic tomosynthesis images are described. Embodiments comprise tomosynthesis systems and methods for creating a reconstructed image of an object from a plurality of two-dimensional x-ray projection images. These systems comprise: an x-ray detector; and an x-ray source capable of emitting x-rays directed at the x-ray detector; wherein the tomosynthesis system utilizes asymmetric image acquisition geometry, where $\theta_1 \neq \theta_0$, during image acquisition, wherein $\theta_1$ is a sweep angle on one side of a center line of the x-ray detector, and $\theta_0$ is a sweep angle on an opposite side of the center line of the x-ray detector, and wherein the total sweep angle, $\theta_{asym}$, is $\theta_{asym} = \theta_1 + \theta_0$. Reconstruction algorithms may be utilized to produce reconstructed images of the object from the plurality of two-dimensional x-ray projection images.

20 Claims, 8 Drawing Sheets

RADIOGRAPHIC TOMOSYNTHESIS IMAGE ACQUISITION UTILIZING ASYMMETRIC GEOMETRY

FIELD OF THE INVENTION

The present invention relates generally to radiographic tomosynthesis image acquisition. More specifically, the present invention relates to systems and methods that provide better slice sensitivity and image quality than currently possible with existing radiographic tomosynthesis systems and methods. Even more specifically, the present invention relates to radiographic tomosynthesis systems and methods that utilize asymmetric geometry for image acquisition so as to provide an optimum total sweep angle that maximizes the image quality that can be achieved thereby.

BACKGROUND OF THE INVENTION

Tomosynthesis is an advanced three-dimensional radiographic imaging technique in which several 2-D images of a patient are taken at different angles and/or planes, and then these images are reconstructed as a 3-D image of the volume of the patient that was imaged. Unlike conventional x-ray imaging techniques, radiographic tomosynthesis provides depth information about an area of interest within an object being imaged, such as a tumor or other anatomy within a patient. Tomosynthesis also enables any number of tomographic slices to be reconstructed from a single scanning sequence of x-ray exposures, without requiring additional x-ray imaging, thereby making tomosynthesis a desirable characterization tool.

The two most common tomosynthesis system architectures comprise either a table configuration (i.e., an x-ray tube located above the patient and a digital x-ray detector located underneath the patient) or a wall-stand configuration (i.e., an x-ray tube located in front of the patient and a digital x-ray detector located behind the patient). The x-ray tube generally sweeps along an arc, circle, ellipse, hypocycloid, line, or any other suitable geometry, to generate a series of projection images on the x-ray detector, and then the series of projected images are reconstructed using a 3-D reconstruction algorithm. Collecting images from a variety of angles in this manner allows depth information to be incorporated into the final image. However, due to the height, size, layout, dimensions, etc., of the imaging room, these images can generally only be acquired over a limited area (i.e., normally angles less than 60°), thereby limiting the slice sensitivity and quality of the acquired image data.

Tomosynthesis is generally accomplished utilizing symmetric acquisition geometry. In other words, the sweep angle above and below the center of the x-ray detector, or on one side of the center line of the x-ray detector and on the opposite side of the center line of the x-ray detector, is generally the same. For example, if the dimensions or other limitations of a room only allow enough space to sweep 20 below the center of the x-ray detector, then existing tomosynthesis systems will only sweep 20° above the center of the x-ray detector too so that symmetrical image acquisition is achieved. Therefore, it is clear that the dimensions or other limitations of a room can significantly limit the total sweep angle that is possible in existing tomosynthesis systems. It would be desirable to have tomosynthesis systems that utilize asymmetric image acquisition geometry so that the dimensions, layout, etc., of a room would not be so limiting on the total possible sweep angle. For example, it would be desirable to be able to asymmetrically sweep 30° above and 20 below the center of the x-ray detector, if that is what the room allows.

Since existing tomosynthesis systems and methods have geometric limitations, it would be desirable to have tomosynthesis systems and methods that lack those geometric restrictions. Additionally, it would be desirable to be able to utilize the improved tomosynthesis systems and methods without having to modify the room layout, dimensions, overhead x-ray tube support, x-ray detector support, etc.

SUMMARY OF THE INVENTION

Accordingly, the above-identified shortcomings of existing tomosynthesis systems and methods are overcome by embodiments of the present invention, which relates to radiographic tomosynthesis systems and methods that utilize asymmetric image acquisition geometry. The asymmetric image acquisition geometry utilized by this invention yields higher slice sensitivity and better image quality than currently possible with existing radiographic tomosynthesis systems and methods.

Embodiments of this invention comprise tomosynthesis systems and methods for creating a reconstructed image of an object from a plurality of two-dimensional x-ray projection images. These systems comprise: an x-ray detector; and an x-ray source capable of emitting x-rays directed at the x-ray detector, wherein the tomosynthesis system utilizes asymmetric image acquisition geometry, where $\theta_1 \neq \theta_0$, during image acquisition, wherein $\theta_1$ is a sweep angle on one side of a center line of the x-ray detector, and $\theta_0$ is a sweep angle on an opposite side of the center line of the x-ray detector, and wherein the total sweep angle ($\phi_{asym}$) is $\phi_{asym} = \theta_1 + \theta_0$. In some embodiments, $\theta_{asym}$ is about 40° to about 60°.

In embodiments, the x-ray detector may be positioned at a predetermined position so that images of a region of interest, as acquired during a sweep, are centered on a center of the x-ray detector. This predetermined position may comprise the center of a patient's sternum, a location above the center of the patient's sternum, a location below the center of the patient's sternum, at a patient's stomach; at one or more of a patient's extremities; at a patient's limb; and/or or any other suitable location. The x-ray detector may be tilted so as to be aimed at a center position of the total sweep angle ($\phi_{asym}$), or to be aimed at another predetermined location.

Either one or both of the x-ray source and the x-ray detector may move, in any suitable manner, during image acquisition, such as for example: along a one-dimensional path, along a two-dimensional path, along a three-dimensional path, along an arc, along at least a portion of a circle, along at least a portion of an ellipse, along at least a portion of a hypocycloid, along at least a portion of a line, along at least a portion of a sphere, and/or along at least a portion of a cone.

In embodiments, the x-ray detector may remain stationary during image acquisition. In embodiments, the object being imaged may move during image acquisition, while both the x-ray source and the x-ray detector remain stationary during image acquisition. In still other embodiments, either one or both of the x-ray source and the x-ray detector may move in a translational or rotational manner during image acquisition. X-ray scanning may occur in any suitable direction, such as vertically, horizontally, obliquely, or in any other suitable direction.

A reconstruction algorithm may be utilized to produce a reconstructed image of the object from the plurality of two-dimensional x-ray projection images that are obtained during imaging.

Further features, aspects and advantages of the present invention will be more readily apparent to those skilled in the art during the course of the following description, wherein references are made to the accompanying figures which illustrate some preferred forms of the present invention, and wherein like characters of reference designate like parts throughout the drawings.

DESCRIPTION OF THE DRAWINGS

The systems and methods of the present invention are described herein below with reference to various figures, in which.

DETAILED DESCRIPTION OF THE INVENTION

For the purposes of promoting an understanding of the invention, reference will now be made to some preferred embodiments of the present invention as illustrated in FIGS. 1–8 and specific language used to describe the same. The terminology used herein is for the purpose of description, not limitation. Specific structural and functional details disclosed herein are not to be interpreted as limiting, but merely as a basis for the claims as a representative basis for teaching one skilled in the art to variously employ the present invention. Any modifications or variations in the depicted support structures and methods, and such further applications of the principles of the invention as illustrated herein, as would normally occur to one skilled in the art, are considered to be within the spirit of this invention.

This invention relates to improved tomosynthesis systems and methods that overcome the image acquisition geometric restrictions that exist in current tomosynthesis systems and methods. This invention utilizes asymmetric image acquisition geometry to optimize the total sweep angle during image acquisition, thereby increasing the slice sensitivity (or cross-plane spatial resolution), which yields better image quality in the final images generated therefrom.

Figure 1:
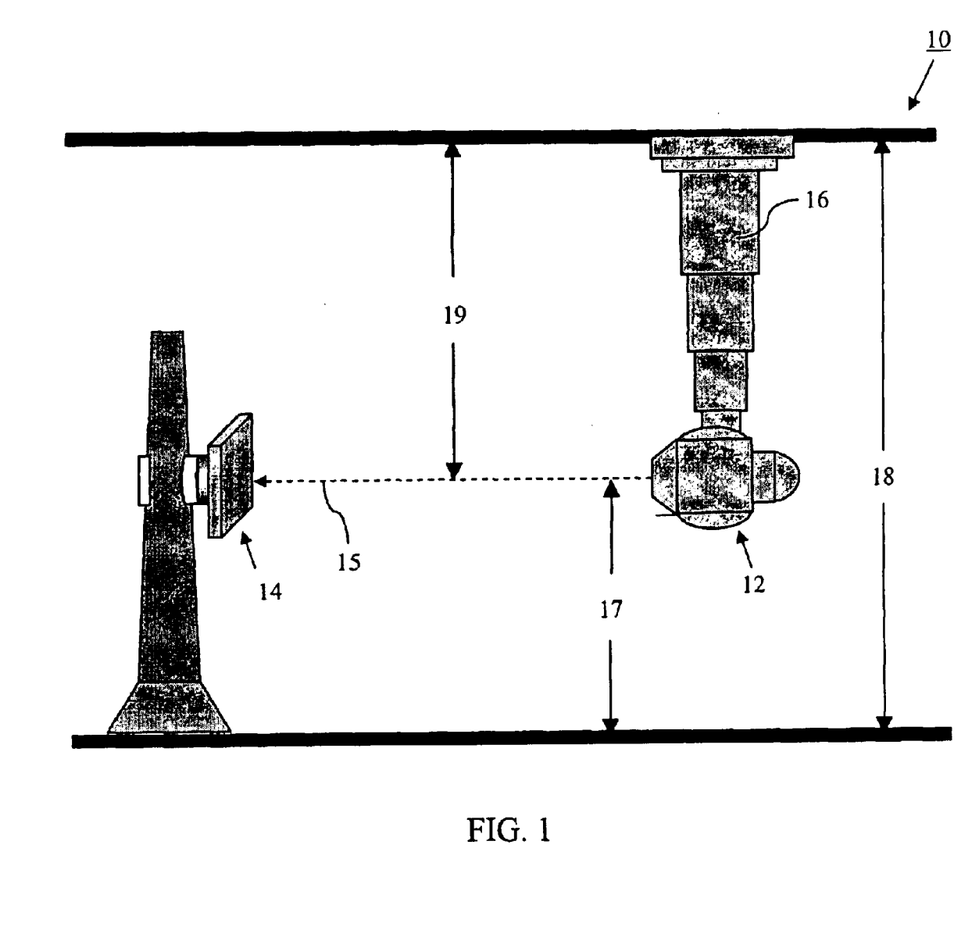
FIG. 1 is a schematic drawing showing the room layout of an exemplary wall-stand configuration of a radiographic tomosynthesis system as utilized in embodiments of this invention.
Figure 3:
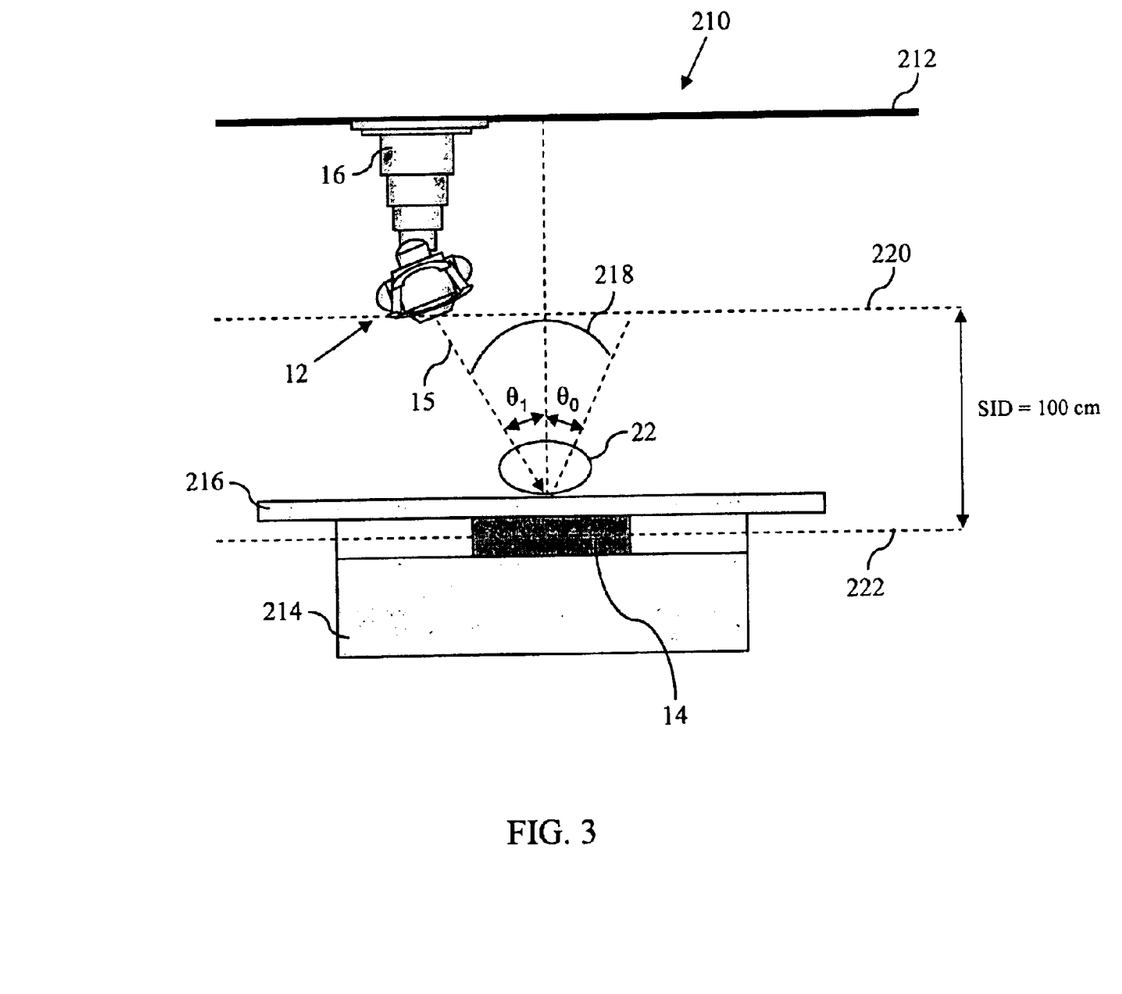
FIG. 3 is a schematic drawing showing the room layout of an exemplary table configuration of a radiographic tomosynthesis system as utilized in embodiments of this invention.

Two typical configurations of systems embodying this invention are shown in FIGS. 1 and 3. Referring first to FIG. 1, there is shown a schematic diagram showing the room layout of one exemplary wall-stand configuration of a radiographic tomosynthesis system 10 as utilized in embodiments of this invention. Such systems 10 generally comprise an x-ray source 12 that projects a beam of x-rays 15 toward an x-ray detector 14, which is disposed in an imaging plane with x-ray source 12. The x-ray detector 14 senses and detects the x-rays that pass through an object 22, such as a patient, that is disposed between the x-ray source 12 and the x-ray detector 14 proximate the x-ray detector 14. An associated control system 150 obtains the detected x-ray energy from the x-ray detector 14, and then, based on the digital signals it receives relating to the intensity of the detected x-rays, prepares a corresponding diagnostic image on a display. An overhead x-ray tube support 16 supports x-ray source 12 so that x-rays 15 from x-ray source 12 can be directed toward the x-ray detector 14. In this embodiment, overhead x-ray support 16 can move telescopically up and down during operation to obtain a series of projection images over a predetermined distance, while x-ray detector 14 remains stationary at a predetermined location. In various alternative embodiments, the x-ray source 12 could remain stationary, and the x-ray detector 14 could move during operation; or both the x-ray source 12 and the x-ray detector 14 could remain stationary, while the patient could move during operation. While this embodiment shows an overhead x-ray tube support 16 hanging from the ceiling, and an x-ray detector 14 being supported by a column rising from the floor, numerous other arrangements are possible (i.e., an arm mounted on a wall could support either the x-ray tube support 16 or the x-ray detector 14, or the x-ray detector 14 could be hanging from the ceiling in some manner, etc.) and all are intended to be covered by this invention.

Figure 2:
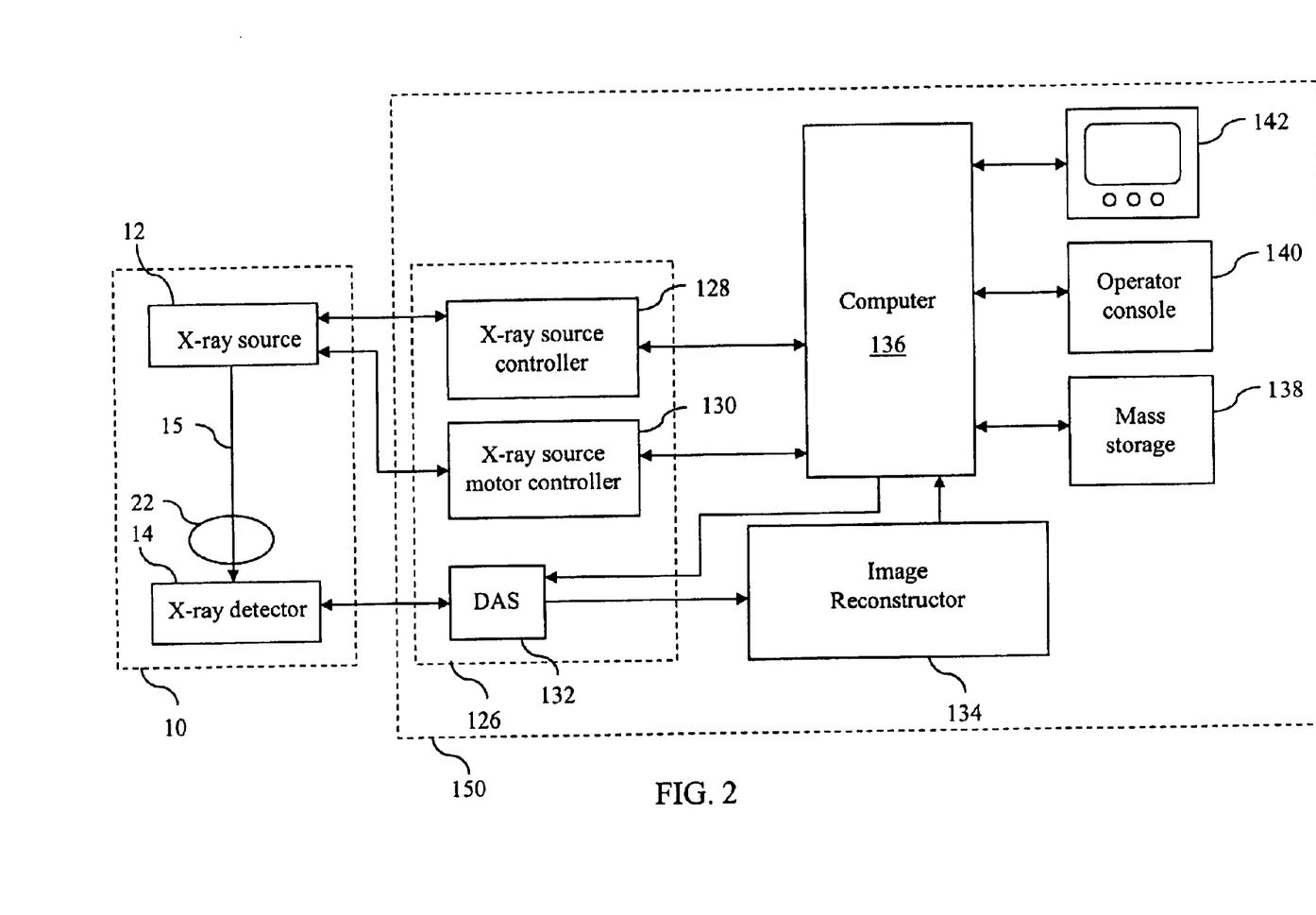
FIG. 2 is a schematic diagram showing the architecture of the tomosynthesis system shown in FIG. 1.

Referring now to FIG. 2, there is shown a schematic diagram showing the architecture of the tomosynthesis system 10 shown in FIG. 1. The operation and movement of x-ray source 12 are governed by a control mechanism 126 of the tomosynthesis system. Control mechanism 126 includes an x-ray source controller 128 that provides power and timing signals to x-ray source 12, and an x-ray source motor controller 130 that controls the sweeping speed, position, and projection/shooting angle of x-ray source 12. A data acquisition system (DAS) 132 in control mechanism 126 samples analog data from the x-ray detector 14, and converts that analog data to digital signals for subsequent processing in accordance with the methods and systems of this invention. An image reconstructor 134 receives the sampled and digitized x-ray data from DAS 132 and performs high speed image reconstruction thereon. The reconstructed image is then applied as input to a computer 136, which can store the image in a mass storage device 138. Computer 136 may also retrieve stored images from the mass storage device 138 for later viewing.

Computer 136 may also receive commands and scanning parameters from an operator via an operator console 140, which may comprise a keyboard, touchpad, or other suitable input device. An associated cathode ray tube display 142 (or other suitable display) may allow the operator to view the reconstructed image and other data from computer 136. The operator supplied commands and parameters may be used by computer 136 to provide control signals and information to DAS 132, x-ray source controller 128, and/or x-ray source motor controller 130.

Embodiments of the present invention may make use of software or firmware running on computer 136 to carry out the processing of data in the methods and systems of this invention. A mouse or pointing device may be employed to facilitate the entry of data and/or image locations. Other embodiments of this invention may utilize a general purpose computer or workstation having a memory and/or printing capability for storing or printing images. Suitable memory devices are well known and include, but are not limited to, RAM, diskettes, hard drives and optical media. Embodiments using such stand-alone computers or workstations may receive data from the tomosynthesis system via conventional electronic storage media or via a conventional communication link, and images may then be reconstructed therefrom.

Referring now to FIG. 3, there is shown a schematic diagram showing the room layout of one exemplary table configuration of a radiographic tomosynthesis system 210 as utilized in embodiments of this invention. Such systems 210 generally comprise an x-ray source 12 that projects a beam of x-rays 15 toward an x-ray detector 14, which is disposed in an imaging plane with x-ray source 12. The x-ray detector 14 senses and detects the x-rays that pass through an object 22, such as a patient, that is disposed between the x-ray source 12 and the x-ray detector 14 proximate the x-ray detector 14. An associated control system obtains the detected x-ray energy from the x-ray detector 14, and then, based on the digital signals it receives relating to the intensity of the detected x-rays, prepares a corresponding diagnostic image on a display. An overhead x-ray tube support 16 supports x-ray source 12 so that x-rays 15 from x-ray source 12 can be directed toward the object 22 lying on the table top 216 above the x-ray detector 14. In this embodiment, overhead x-ray support 16 can move horizontally from side-to-side along the ceiling 212 during operation to obtain a series of projection images over a predetermined distance (i.e., sweep angle 218), while x-ray detector 14 remains stationary at a predetermined location. As with the previous embodiment shown in FIG. 1, in various alternative table configuration embodiments, the x-ray source 12 could remain stationary, and the x-ray detector 14 could move during operation; or both the x-ray source 12 and the x-ray detector 14 could remain stationary, while the patient could move during operation. Also as described before, while this embodiment shows an overhead x-ray tube support 16 hanging from the ceiling 212, and an x-ray detector 14 being supported by a table 214 positioned on the floor, numerous other arrangements are possible and all are intended to be covered by this invention. In these table configurations, the SID is the perpendicular source-to-image distance (i.e., the distance between the focal spot plane 220 and the detector plane 222), and SID≈100 cm.

In exiting tomosynthesis systems, symmetric image acquisition geometry is used. However, symmetric geometry is not practical many times, such as when using a wall-stand configuration similar to that shown in FIG. 1, where the travel range of the x-ray tube 12 is limited by the room size/layout. Two factors jointly determine the range of the focal spot height 17 (measured up from the floor) of the x-ray tube in such configurations: the ceiling height 18 (measured up from the floor) and the overhead x-ray tube support extension distance 19 (measured down from the ceiling). Because of these two restrictions, with symmetric geometry, it is difficult to use the desired total sweep angle to perform tomosynthesis on patients taller or shorter than a certain range of heights, and thus the image quality is significantly affected when tomosynthesis is performed on such tall or short patients. In one exemplary, non-limiting embodiment, the ceiling height 18 is approximately 9'5" (2896 mm); the minimum overhead x-ray tube support extension distance 19 is approximately 31" (787 mm); the maximum overhead x-ray tube support extension distance 19 is approximately 102" (2589 mm); the minimum focal spot height 17 is approximately 11" (309 mm); and the maximum focal spot height 17 is approximately 82" (2109 mm). Numerous other layouts and room dimensions are also possible without deviating from the spirit and scope of this invention.

Figure 4:
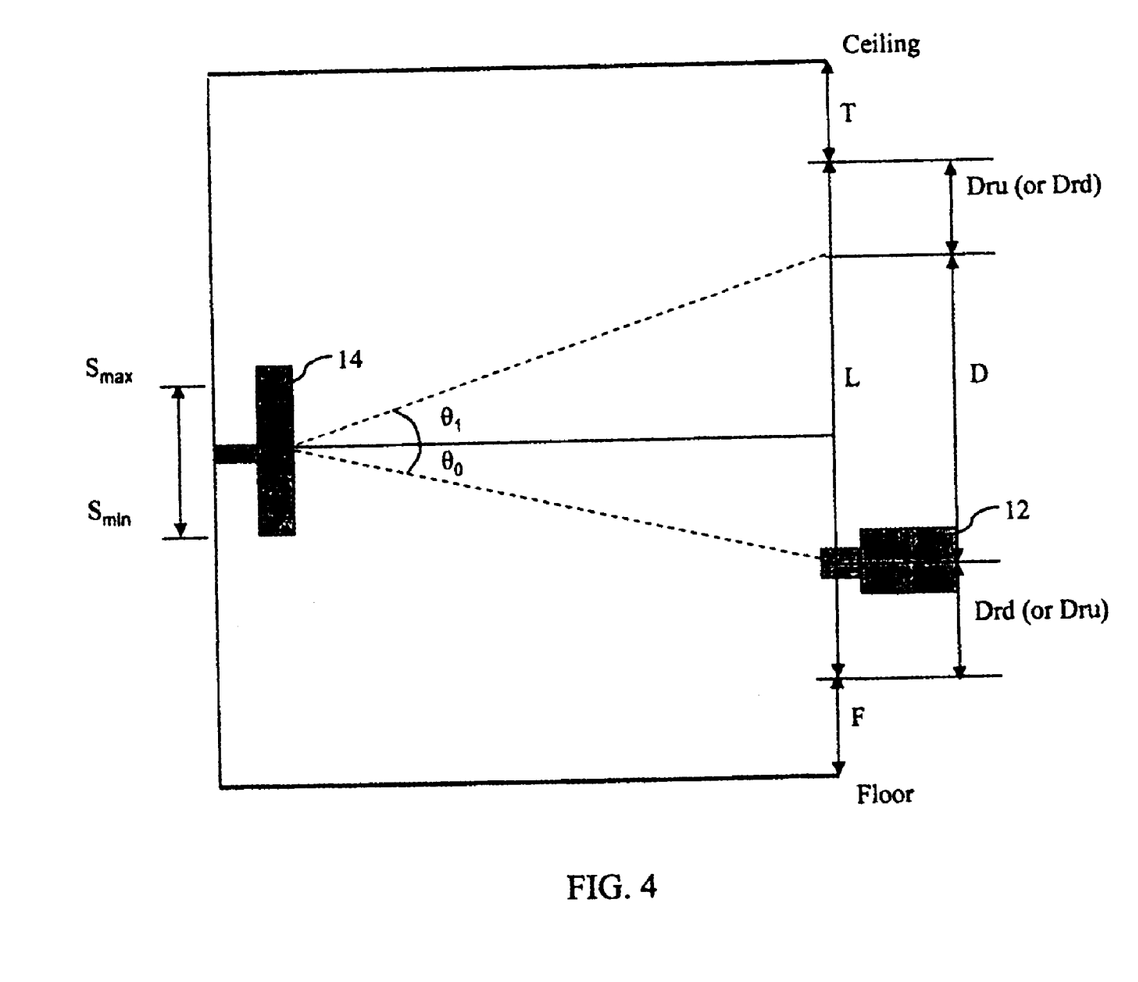
FIG. 4 is a schematic drawing showing the upper and lower sweeping limits of one embodiment of this invention.

Referring now to FIG. 4, there is shown a schematic drawing showing the upper and lower sweeping limits, due to the dimensions and layout of the room, of the embodiment of this invention depicted in FIG. 1. In this invention, if the sweep angle below the center of the x-ray detector, $\theta_0$, is limited to 20°, but the sweep angle above the center of the x-ray detector, $\theta_1$, can be 30°, then it would be desirable to be able to utilize asymmetric acquisition geometry to take advantage of that fact. In such a case, the total sweep angle on existing tomosynthesis systems would be 40°, since the sweep angle both above and below the center of the x-ray detector would be limited to 20° each, for a total of 40°; but with the present invention, the total sweep angle would be 50°, because it would be possible to sweep 30° above and 20° below the center of the x-ray detector, for a total of 50°. By allowing a greater total sweep angle than possible with existing tomosynthesis systems and methods, improved slice sensitivity and image quality can be achieved with the present invention.

Now in more detail, and referring still to FIGS. 1 and 4, during tomosynthesis, a patient may stand in a predetermined position, such as with their back against the x-ray detector 14, and the center of x-ray source 12 can be positioned at a desired location, such as at the patient's sternum (i.e., at the center of the patient's chest). The x-ray source 12 travels vertically up and/or down while exposures are taken. The vertical travel distance (D) of the x-ray source 12 is equal to the focal spot height range (L) minus the distances needed for the x-ray source 12 to ramp up (Dru) and ramp down (Drd). In this invention, $$D = L - Dru - Drd. \tag{1}$$

Given a sternum height (S), which falls in a range between $S_{min}$ and $S_{max}$, we have:

$$S = (L+F) - Dru - SID*\tan(\theta_1) \tag{2}$$

and $$S = F + Drd + SID*\tan(\theta_0) \tag{3}$$

where F is the minimal focal spot height, and SID is the perpendicular source-to-image distance. Herein, T is the minimal overhead x-ray support extension distance.

Equations (2) and (3) can be rewritten as:

$$\theta_1 = atan((L+F-S-Dru)/SID) \tag{4}$$

and $$\theta_0 = atan((S-F-Drd)/SID). \tag{5}$$

The distributions of sternum heights (S) in US adults between the ages of 18 and 64 are as follows:

| Probability (%) | 1 | 10 | 20 | 30 | 40 | 50 | 60 | 70 | 80 | 90 | 99 |
|---|---|---|---|---|---|---|---|---|---|---|---|
| Height (cm) Male | 118 | 125 | 128 | 130 | 132 | 133 | 135 | 137 | 139 | 142 | 150 |
| Height (cm) Female | 100 | 109 | 112 | 114 | 116 | 118 | 122 | 124 | 127 | 129 | 135 |

Using various sternum heights (S) from 80–150 cm, and using SID=180 cm, L=180 cm, F=30.9 cm, Dru=15 cm and Drd=15 cm, 0, and $\theta_0$ can be calculated as a function of S. The results thereof are shown in FIG. 5.

Figure 5:
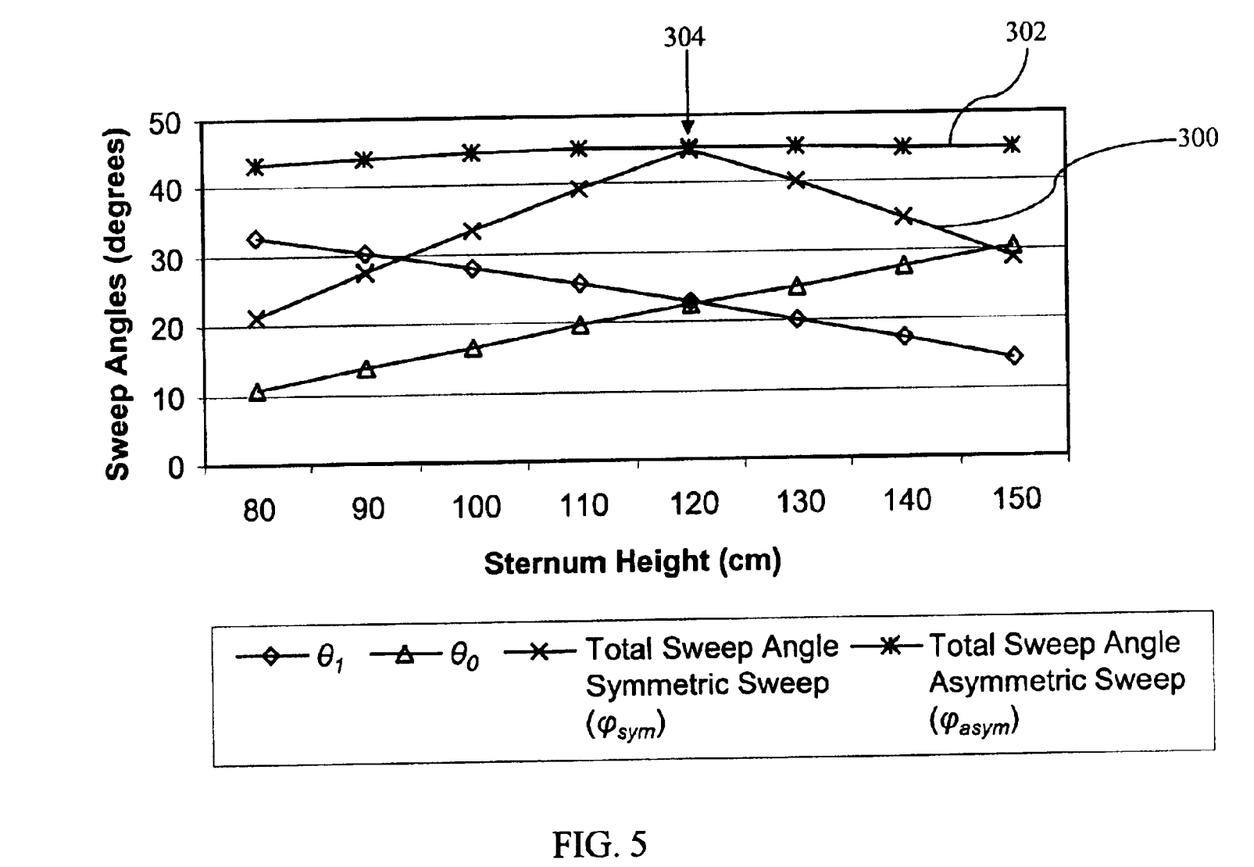
FIG. 5 is a graph showing sweep angles versus sternum heights.

First, utilizing symmetric geometry, where $\theta_1=\theta_0=\theta$, whichever of $\theta_1$ and $\theta_0$ is smaller becomes the dominant limiting factor, and the total sweep angle ($\phi$) is equal to:

$$\phi_{sym}=2\theta=2*\min(\theta_0,\theta_1) \quad (6)$$

which is also shown in FIG. 5 as line 300. Now, utilizing asymmetric geometry, the total sweep angle is equal to:

$$\phi_{asym}=\theta_1+\theta_0 \quad (7)$$

which is also shown in FIG. 5 as line 302. As asymmetric geometry yields the most optimal slice sensitivity achievable, these results shows that, with symmetric acquisition geometry and current tomosynthesis systems and methods, the slice sensitivity of the tomosynthesis images is expected to be less than optimal in about 70% of the male patient population, and less than optimal in about 20% of the female patient population. Additionally, the trend indicates that the slice sensitivity will be less than optimal in an even greater percent of cases for sternum heights less than 80 cm or greater than 150 cm.

Even though it is known that larger total sweep angles can reduce out-of-plane artifacts, it is very difficult to increase the total sweep angle in many cases. In theory, it is possible to increase the total sweep angle by increasing the ceiling height 18 and/or by increasing the overhead x-ray tube support extension distance 19. However, to increase the ceiling height, major renovations would generally be required, and the overhead x-ray tube support extension distance 19 is usually limited by its weight and column stiffness. Therefore, these solutions would significantly increase the development costs and time. Additionally, while it would be possible to stand shorter patients on a stool or raised platform of some sort, and seat taller patients on a stool or chair of some sort, this could complicate the workflow and increase patient discomfort. Therefore, these solutions are also less than ideal. There is no readily apparent solution that offers the same benefits and simplicity as the present invention.

An easier, faster, and less costly solution is to use asymmetric image acquisition geometry with existing tomosynthesis systems, and allow $\theta_0 \neq \theta_1$. Using asymmetric geometry, the total sweep angle is:

$$\phi_{asym}=\theta_1+\theta_0 \quad (7)$$

which is shown in FIG. 5 as line 302. As seen in FIG. 5, the only height where the total sweep angle is optimized in both symmetric and asymmetric image acquisition geometry is for sternum heights of approximately 120 cm 304. For every other sternum height, asymmetric image acquisition geometry yields a greater total sweep angle than symmetric image acquisition geometry yields. Therefore, in all cases other than those where the sternum height is approximately 120 cm, asymmetric image acquisition geometry yields better quality images that have better resolution than those obtained using symmetric image acquisition geometry.

The benefits of asymmetric image acquisition geometry are threefold: (1) the desired total sweep angle can be achieved for patients of almost all heights, thereby improving the image quality for virtually everyone; (2) almost the same total sweep angle can be used for all patients, thereby improving the consistency of the image quality among patients; (3) the asymmetric image acquisition geometry can actually allow the total sweep angle to be increased over what conventional symmetric image acquisition geometry would allow for most patient heights, without requiring physical modifications to the tomosynthesis system and/or tomosynthesis room.

This invention also allows the slice sensitivity to be optimized. The slice sensitivity, or cross-plane spatial resolution, of a tomosynthesis system describes the system's ability to resolve objects in different tomographic planes. Slice sensitivity is the key differentiator between radiographic tomosynthesis and conventional radiographs. Higher slice sensitivity has less out-of-plane artifacts in the reconstructed images, and therefore, results in better image quality. Therefore, it is desirable to have tomosynthesis systems that have high slice sensitivity.

Figure 6:
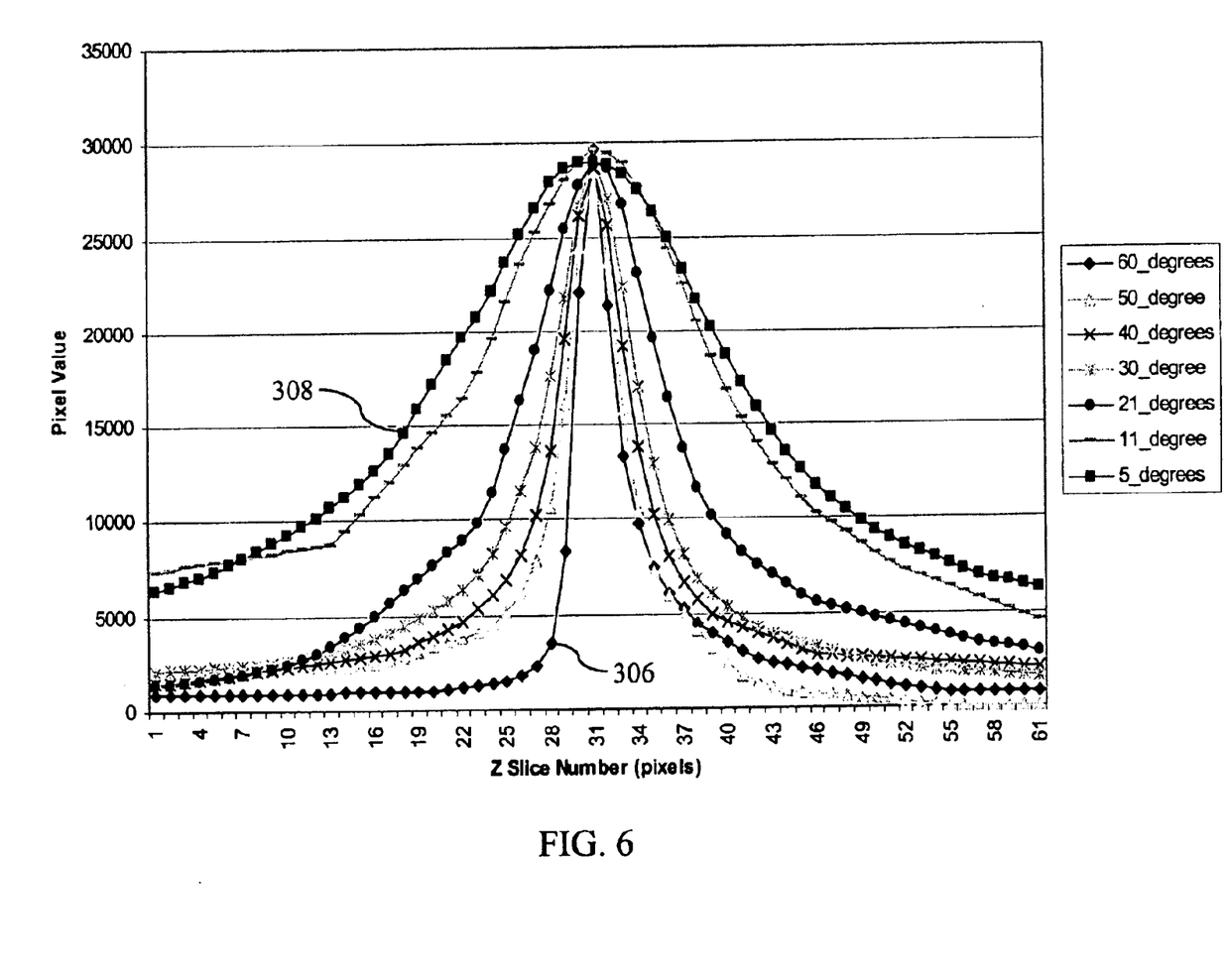
FIG. 6 is a graph showing slice sensitivity versus sweep angle for a 1-pixel wire.
Figure 7:
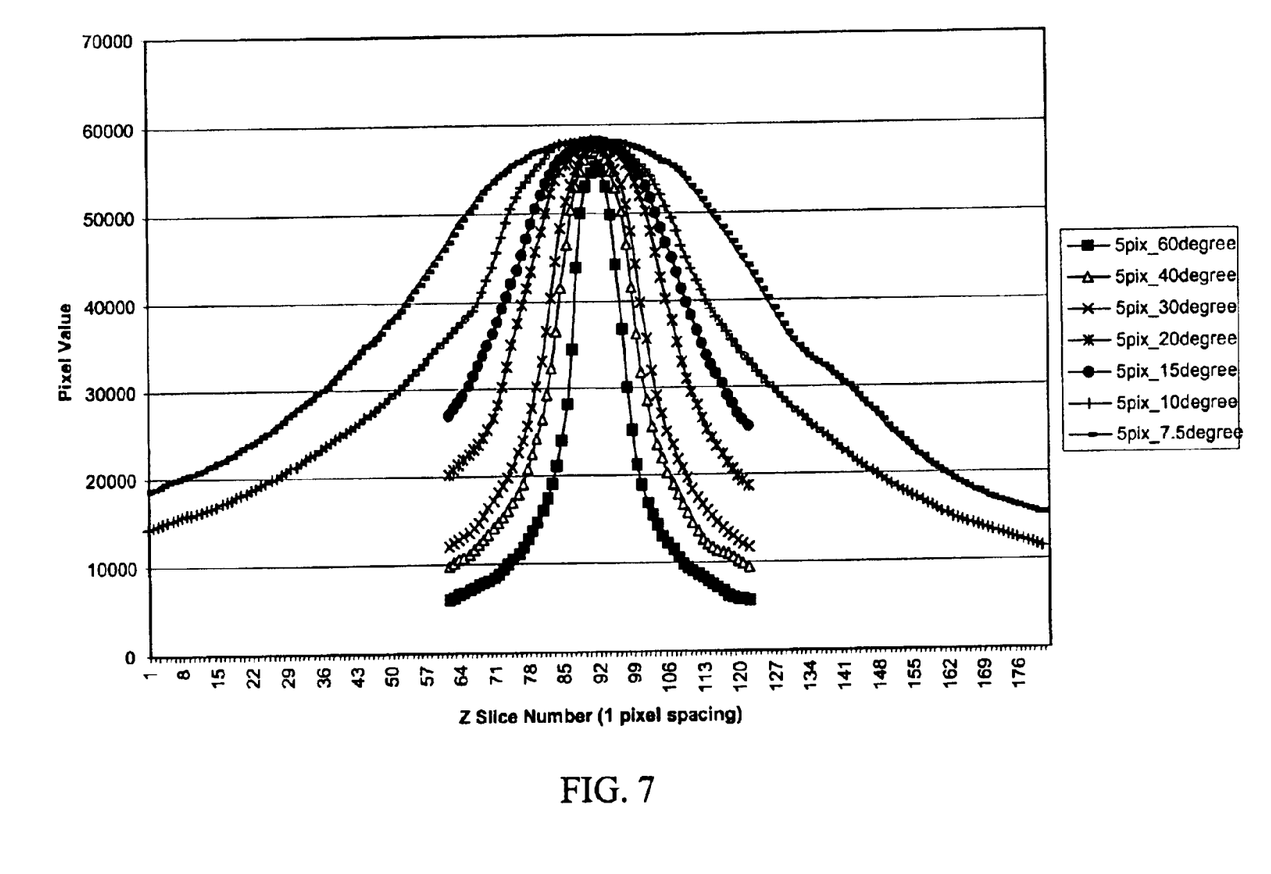
FIG. 7 is a graph showing slice sensitivity versus sweep angle for a 5-pixel wire.

FIGS. 6 and 7 show the results of the slice sensitivity profiles over a variety of sweep angles for two computer simulated wire phantoms, the diameters of which are 1 and 5 pixels, respectively. In FIGS. 6 and 7, the narrower the curve, the better the slice sensitivity and resolution in the final image. Therefore, FIGS. 6 and 7 quantitatively show that the slice sensitivity increases with an increase of the sweep angle. For example, as seen in FIG. 6, the curve for the 60° total sweep angle 306 is much narrower than the curve for the 5° total sweep angle 308, indicating that the slice sensitivity for the 60° total sweep angle is higher than that for the 5° total sweep angle, therefore indicating that the 60° total sweep angle will yield a final image having better resolution than the 5° total sweep angle will yield.

Figure 8:
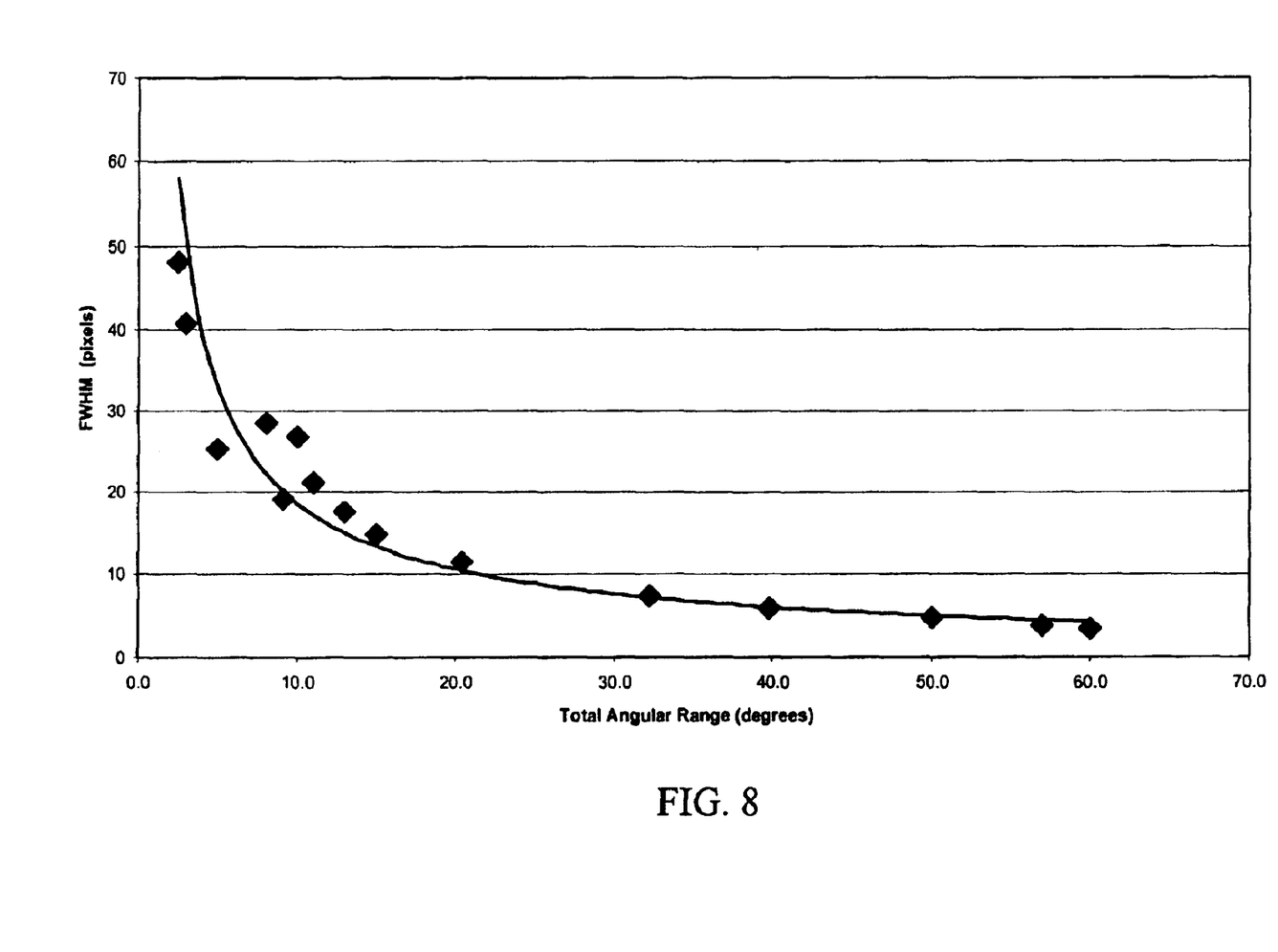
FIG. 8 is a graph showing full-width-at-half-maximum versus sweep angle for the 1-pixel wire shown in FIG. 6.

FIG. 8 is a graph showing full-width-at-half-maximum versus sweep angle for the 1-pixel wire depicted in FIG. 6. On the y-axis, the lower the FWHM or z-resolution, the better the resolution in the final image. This figure shows that the slice sensitivity is close to being optimized using asymmetric image acquisition geometry when the total sweep angle is somewhere between about 40° and about 60°. Therefore, in some non-limiting embodiments, the desired total sweep angle is about 40–60°, in others it is about 40–50°, in still others it is about 40–45°, and in yet others it is about 43–44°. However, the total sweep angle may be optimized differently for different tomosynthesis systems, and therefore, no limitation is hereby intended by these ranges.

Various minor adjustments can be made to the tomosynthesis systems of the present invention, if necessary or desired, to help improve the image quality. For example, if the x-ray source 12 is higher or lower than the sternum height (S) for more than 50 percent of its total vertical travel distance (D), the x-ray detector 14 could be positioned lower or higher, respectively, than S, so that the images of the region of interest (i.e., the sternum region of the patient) during the sweep are centered around the center of the x-ray detector 14. Additionally or alternatively, it may also be beneficial in some cases to tilt the x-ray detector 14 so it is aimed at the center position of the sweep.

As described above, this invention allows higher quality tomosynthesis images, having better cross-plane spatial resolution, to be achieved than is currently possible with existing tomosynthesis systems and methods. Advantageously, only minor modifications, if any, to existing tomosynthesis systems are needed to practice this invention, thereby making this solution particularly attractive. Many other advantages will also be apparent to those skilled in the relevant art.

Various embodiments of this invention have been described in fulfillment of the various needs that the invention meets. It should be recognized that these embodiments are merely illustrative of the principles of various embodiments of the present invention. Numerous modifications and adaptations thereof will be apparent to those skilled in the art without departing from the spirit and scope of the present invention. The techniques of this invention may be performed in numerous different ways without varying from the spirit and scope of this invention, and all such variations are intended to be covered herein. For example, while a wall-stand configuration was discussed herein in detail, this invention could also be utilized with a table configuration or any other suitable configuration. Thus, it is intended that the present invention cover all suitable modifications and variations as come within the scope of the appended claims and their equivalents.

What is claimed is:

1. A tomosynthesis system for creating a reconstructed image of an object from a plurality of two-dimensional x-ray projection images, the system comprising:
   an x-ray detector;
   an x-ray source capable of emitting x-rays directed at the x-ray detector, wherein the tomosynthesis system utilizes asymmetric image acquisition geometry, where $\theta_1 \neq \theta_0$, during image acquisition, wherein $\theta_1$ is a sweep angle on one side of a center line of the x-ray detector, and $\theta_0$ is a sweep angle on an opposite side of the center line of the x-ray detector;
   wherein the total sweep angle ($\phi_{asym}$) is: $\phi_{asym} = \theta_1 + \theta_0$; and wherein $\phi_{asym}$ is about 40° to about 60°.

2. The tomosynthesis system of claim 1, wherein the x-ray detector is positioned at a predetermined position so that images of a region of interest, as acquired during a sweep, are centered on a center of the x-ray detector.

3. The tomosynthesis system of claim 2, wherein the predetermined position comprises at least one of: at a center of a patient's sternum, above the center of the patient's sternum; below the center of the patient's sternum; at a patient's stomach; at one or more of a patient's extremities; and at a patient's limb.

4. The tomosynthesis system of claim 1, wherein at least one of the x-ray source and the x-ray detector moves during image acquisition.

5. The tomosynthesis system of claim 4, wherein at least one of the x-ray source and the x-ray detector moves in at least one of the following manners during image acquisition: along a one-dimensional path, along a two-dimensional path, along a three-dimensional path, along an arc, along at least a portion of a circle, along at least a portion of an ellipse, along at least a portion of a hypocycloid, along at least a portion of a line, along at least a portion of a sphere, and along at least a portion of a cone.

6. The tomosynthesis system of claim 1, wherein the x-ray detector remains stationary during image acquisition.

7. The tomosynthesis system of claim 1, wherein the object being imaged moves during image acquisition, while both the x-ray source and the x-ray detector remain stationary during image acquisition.

8. The tomosynthesis system of claim 1, wherein at least one of the x-ray source and the x-ray detector moves in a translational or rotational manner during image acquisition.

9. The tomosynthesis system of claim 1, wherein x-ray scanning occurs in at least one of the following directions: vertically, horizontally, and obliquely.

10. The tomosynthesis system of claim 1, wherein a reconstruction algorithm produces a reconstructed image of the object from the plurality of two-dimensional x-ray projection images.

11. A tomosynthesis method for creating a reconstructed image of an object from a plurality of two-dimensional x-ray projection images, the method comprising:
    providing an x-ray detector;
    providing an x-ray source capable of emitting x-rays directed at the x-ray detector;
    utilizing asymmetric image acquisition geometry, where $\theta_1 \neq \theta_0$, during image acquisition, wherein $\theta_1$ is a sweep angle on one side of a center line of the x-ray detector, and $\theta_0$ is a sweep angle on an opposite side of the center line of the x-ray detector;
    wherein the total sweet, angle ($\phi_{asym}$) is $\phi_{asym} = \theta_1 + \theta_0$; and wherein $\phi_{asym}$ is about 40° to about 60°.

12. The tomosynthesis method of claim 11, further comprising:
    positioning the x-ray detector at a predetermined position so that images of a region of interest, as acquired during a sweep, are centered on a center of the x-ray detector.

13. The tomosynthesis method of claim 12, wherein the predetermined position comprises at least one of: at a center of a patient's sternum, above the center of the patient's sternum; below the center of the patient's sternum; at a patient's stomach; at one or more of a patient's extremities; and at a patient's limb.

14. The tomosynthesis method of claim 11, further comprising:
    moving at least one of the x-ray source and the x-ray detector during image acquisition.

15. The tomosynthesis method of claim 14, further comprising:
    moving at least one of the x-ray source and the x-ray detector in at least one of the following manners during image acquisition: along a one-dimensional path, along a two-dimensional path, along a three-dimensional path, along an arc, along at least a portion of a circle, along at least a portion of an ellipse, along at least a portion of a hypocycloid, along at least a portion of a line, along at least a portion of a sphere, and along at least a portion of a cone.

16. The tomosynthesis method of claim 11, further comprising:
    holding the x-ray detector stationary during image acquisition.

17. The tomosynthesis method of claim 11, further comprising:
    moving the object being imaged during image acquisition, while holding both the x-ray source and the x-ray detector stationary during image acquisition.

18. The tomosynthesis method of claim 11, further comprising:
    moving at least one of the x-ray source and the x-ray detector in a translational or rotational manner during image acquisition.

19. The tomosynthesis method of claim 11, wherein x-ray scanning occurs in at least one of the following directions: vertically, horizontally, and obliquely.

20. The tomosynthesis method of claim 11, further comprising: utilizing a reconstruction algorithm to produce a reconstructed image of the object from the plurality of two-dimensional x-ray projection images.

\* \* \* \* \*